United States Patent [19]

Schlicht et al.

[11] 4,003,720
[45] Jan. 18, 1977

[54] TELOMERIC-HYDROCARBON PHOSPHORUS COMPOUND AND HYDROCARBON COMPOSITION CONTAINING SAME

[75] Inventors: Raymond C. Schlicht, Fishkill; Justin C. Powell, Wappingers Falls, both of N.Y.

[73] Assignee: Texaco Inc., New York, N.Y.

[22] Filed: June 11, 1975

[21] Appl. No.: 585,943

[52] U.S. Cl. .................. 44/76; 44/DIG. 1; 44/DIG. 4

[51] Int. Cl.² .......................... C10L 1/26

[58] Field of Search ............ 44/76, DIG. 4, DIG. 1; 260/502.4 R

[56] References Cited

UNITED STATES PATENTS

| 2,230,371 | 2/1941 | Bolton | 260/502.4 |
| 2,311,306 | 2/1943 | Ritchey | 260/502.4 P |

Primary Examiner—Daniel E. Wyman
Assistant Examiner—Y. Harris-Smith
Attorney, Agent, or Firm—T. H. Whaley; C. G. Ries; James J. O'Loughlin

[57] ABSTRACT

Telomeric hydrocarbon phosphorus compounds and hydrocarbon compositions containing said compounds are described. The telomeric hydrocarbon phosphorus compounds are represented by the formula:

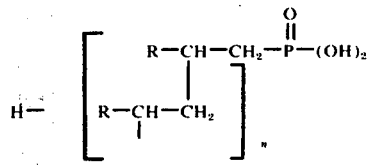

in which R is a hydrocarbon radical having from 1 to 18 carbon atoms and $n$ has a value from 0 to 100.

4 Claims, No Drawings

TELOMERIC-HYDROCARBON PHOSPHORUS COMPOUND AND HYDROCARBON COMPOSITION CONTAINING SAME

BACKGROUND OF THE INVENTION

1. Field of the Invention

Modern internal combustion engine design is undergoing important changes to meet stricter standards concerning engine and exhaust gas emissions. One major change in engine design adopted is the feeding of blow-by gases from the crankcase zone of the engine into the intake air-fuel mixture at the carburetor just below the throttle plate rather than venting these gases to the atmosphere as in the past. The blow-by gases contain substantial amounts of deposit-forming substances and are known to form deposits in and around the throttle plate area of the carburetor. Another significant change is the recirculation of a part of the exhaust gases to the fuel-air intake of the engine. The exhaust gases also have deposit-forming tendencies. The deposits caused by the recirculated gases, both blow-by and exhaust gases, restrict the flow of air through the carburetor at idle and at low speeds, and an overrich fuel mixture results. This condition produces rough engine idling and stalling and leads to the release of excessive hydrocarbon exhaust emissions to the atmosphere.

Phosphorus compounds have heretofore been disclosed for use in a motor fuel composition both as deposit modifiers to inhibit preignition in the engine and as surface active agents to reduce carburetor icing problems. As a result of recent environmental developments, regulations have been promulgated directed to the level of phosphorus which can be present in a motor fuel composition. The Environmental Protection Agency has issued a standard for such a fuel which specifies that "unleaded gasoline" and, by implication, a phosphorus-free gasoline "means gasoline containing not more than 0.05 gram of lead per gallon and not more than 0.005 gram of phosphorus per gallon." Many of the known phosphorus fuel additives are ineffective for their intended purpose in gasoline at such a low concentration.

Telomeric phosphorus compounds are obtained in a reaction wherein an olefin is telomerized in the presence of a phosphorus containing free radical until a plurality of olefin monomers have been so reacted. As indicated, the reaction resembles polymerization in that olefin monomers can be continuously fed to the reaction until a telomeric phosphorus compound of desired properties has been obtained at which time the reaction is stopped.

DESCRIPTION OF THE PRIOR ART

U.S. Pat. No. 3,578,595 and Canadian Pat. No. 907,595 disclose mineral lubricating oil compositions containing n-alkanephosphonic acid type additives as friction modifiers in an automatic transmission fluid.

SUMMARY OF THE INVENTION

The additive of the invention which exhibits surface active properties and which imparts valuable properties to a motor fuel composition in the gasoline boiling range is a telomeric phosphorus compound represented by the formula:

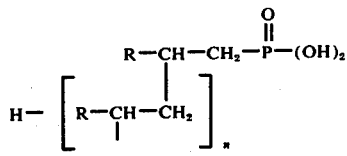

in which R is a hydrocarbon radical having from 1 to 18 carbon atoms and $n$ has a value from 0 to 100 with the average value of $n$ for the composition being greater than 0.5.

A preferred class of telomeric phosphorus additives for the purpose disclosed is one in which R is an aliphatic hydrocarbon radical having from 6 to 18 carbon atoms and $n$ has an average value from about 1 to 25. Still more preferred are those compounds in which R is an aliphatic radical having from 10 to 16 carbon atoms and $n$ has an average value from 2 to 10.

The telomeric phosphorus compound employed in this invention is produced in an addition reaction between a phosphorus containing nucleus or free radical and a monoolefinic hydrocarbon in molecular proportions of from about 2 to 100 moles of said olefinic hydrocarbon permole of said phosphorus containing reactant. A catalyst, such as t-butyl peroxide, is employed as a reaction initiator forming a free radical containing phosphorus. This is caused to react with the olefin monomer to the desired extent, after which the chain reaction is terminated. This sequence of reactions is illustrated as follows:

<u>Reaction Initiation:</u>

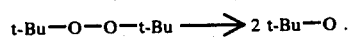

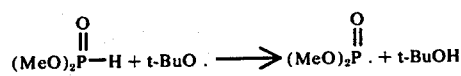

<u>Chain Reaction</u>

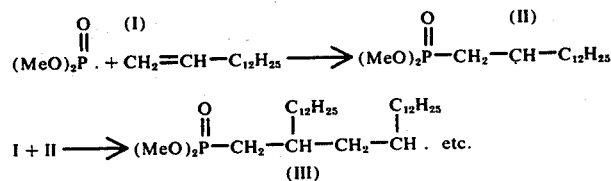

The above chain reaction continues until terminated, usually by abstracting an H. from

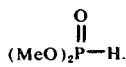

The resultant telomer,

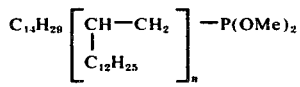

is readily converted to the corresponding

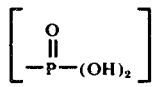

group as desired. Alkyl ester intermediates may be present in the final phosphonic acid composition due to incomplete hydrolysis; however, the phosphonic acids are the active components of the invention.

Suitable phosphorus containing reactants include the $C_1$ to $C_3$ dialkyl phosphites such as dimethyl phosphite, diethyl phosphite, and di-n-propyl phosphite.

The olefinic hydrocarbons which can be employed for preparing the telomeric alkane phosphonates of the invention include both the normal and branched chain olefins having from 3 to 20 carbon atoms. The preferred olefins for this process are the aliphatic olefins having from 6 to about 18 carbon atoms. Examples of effective monoolefins for the purpose disclosed include propylene, 1-butene, isobutylene, 1-pentene, isopentene, 1-hexene, 1-heptene, 1-octene, 1-decene, 1-dodecene, 1-tetradecene and 1-hexadecene.

In general, those monoolefins having the olefinic bond in a terminal location, such as the normal 1-olefins, are most effective for the present process.

The following examples illustrate the preparation of telomeric phosphorus compounds.

EXAMPLE I

Synthesis of a Telomeric Dimethyl Hydrocarbyl Phosphonate (Charging a 2:1 mole ratio of Tetradecene : Dimethyl Phosphite)

A mixture of 392 g. (2.0 mole) tetradecene-1 and 110 g. (1.0 mole) dimethyl phosphite was heated to 300° F. under a $N_2$ atmosphere. Then 4.0 g. di-t-butyl-peroxide (t-$Bu_2O_2$) were added dropwise over 20 min. After 3 hrs. at 300°–310° F., another 4 g. of t-$Bu_2O_2$ were added over 10 min. After another 3 hrs. at 300°–310° F. the mixture was cooled somewhat and then distilled at about 15 mmHg. pressure to a pot temperature of 390° F. to remove 100 g. unreacted olefin and phosphite. The 395 g. crude product contained 6.69% P and had 462 mol. wt. (vs. 6.1% and 502 calculated for a 2:1 telomer). The crude product was then distilled at 4 mmHg. pressure to a pot temperature of 295° C. The 162 g. distillate presumed to be composed largely of the non-telomeric, 1:1 adduct, boiled at 180°–220° C. The yield of telomeric ester product (the pot residue) was 218 g. Analyses of the telomeric ester pot residue were as follows:

|  | %P | %C | %H | Mol. Wt. | Iodine No. |
| --- | --- | --- | --- | --- | --- |
| Found | 5.29 | 73.6 | 13.0 | 935 | 5.5 |
| Calculated for 2:1 telomer | 6.18 | 71.8 | 12.5 | 502 | 0 |

The phosphorus analysis indicates the product to be a 586 mol. wt. telomer having an average of 2.5 tetradecene groups per phosphorus atom.

EXAMPLE II

Synthesis of a Telomeric Hydrocarbyl Phosphonic Acid from a 2.5:1 Tetradecene:Dimethyl Phosphonate Telomer Into 100 g. (0.17 mole) of the 2.5:1 telomeric ester of Ex. I, was stirred a mixture of 100 ml. conc. HCl (37%) and 100 ml. water. The reaction mixture was stirred 6 hours at reflux (100°–109° C.). The mixture was cooled, diluted with ethyl ether, and the partially spent aqueous acid phase was separated. Water-washing of the ether phase followed by stripping in vacuo gave 99 g. product. The analyses were as follows:

|  | %P | Mol. Wt. |
| --- | --- | --- |
| Found | 3.6 | 988 |
| Calculated for 6:1 telomer | 2.4 | 1280 |

EXAMPLE III

Synthesis of a Telomeric Dimethyl Hydrocarbyl Phosphonate (Charging a 6:1 Mole Ratio of Tetradecene:Dimethyl Phosphite)

This procedure differs from Ex. I in the use of higher reactant ratio, and the addition of the peroxide (at a higher ratio to the phosphite, but only slightly lower wt. % of entire mixture) in one step but over a longer period of time. Thus, 8 g. di-t-butyl-peroxide were added over 1 hr. to a mixture of 352 g. (1.8 mole) tetradecene-1 and 33 g. (0.3 mole) dimethyl phosphite heated at 300° F. under a $N_2$ atmosphere. After completing the addition, the mixture was held at 300° F. for 6 hours (same total time as in Ex. I). Distillation at 15 mmHg. gave 170 g. crude product (and 211 g. unreacted olefin and phosphite). The crude product on distillation at 1 mmHg. gave 129 g. pot residue (and only 32 g. of distillate, considered to be the non-telomeric 1:1 product). The telomeric ester pot residue gave the following analysis:

|  | %P | Mol. Wt. |
| --- | --- | --- |
| Found | 3.6 | 988 |
| Calculated for 6:1 telomer | 2.4 | 1280 |

On the basis of the phosphorus analysis, the telomeric product has a calculated mol. wt. of 861 with 3.9 tetradecyl groups per phosphorus atom.

EXAMPLE IV

Synthesis of a Telomeric Hydrocarbyl Phosphonic Acid from a 3.9:1 Tetradecene:Dimethyl Phosphonate Telomer A 119 g. portion of the telomeric dimethyl hydrocarbyl phosphonate of Ex. III was converted to its corresponding hydrocarbyl phosphonic acid by treatment with 75 ml. conc. HCl and 50 ml. water as in Ex. II. The resulting product (118 g.) was found to contain 3.56% P (3.72 calc.) and had a Total Acid Number (TAN) of 86 (134 calc.).

EXAMPLE V

Synthesis of a Telomeric Dimethyl Hydrocarbyl Phosphonate (Charging a 6:1 Mole Ratio of Tetradecene:Dimethyl Phosphite)

This is a variation of Ex. III in which the manner of di-t-butyl-peroxide addition was varied. To a mixture, held at 300° F., of 470 g. (2.4 mole) tetradecene-1 and 44 g. (0.4 mole) dimethyl phosphite, 5 g. of the peroxide were added over ½ hr., followed by a slower addition (over 2½ hrs.) of 10 g. more peroxide. The final mixture was held 4 hrs. more at 300° F. (7 hrs. total). Distillation at 15 mmHg. to 222° C. gave 323 g. crude product and 189 g. distillate (unconsumed reactants). The crude product, on redistillation to 295° C. pot temperature at 2 mmHg., gave 281 g. telomeric ester pot residue (= 87% by wt. of the crude product) and only 35 g. of distillate. Since an analysis of this distillate indicated only 5.7% (vs. 6.1% calculated for the 2:1 telomer), this by-product (and those of Examples I and III) may, in fact, contain appreciable amounts of 2:1 telomer. The higher telomeric mixture in the pot residue gave the following analyses:

|  | %P | %C | %H | Mol. Wt. |
|---|---|---|---|---|
| Found | 3.1 | 79.4 | 13.8 | 984 |
| Calculated for 6:1 telomer | 2.4 | 80.7 | 13.7 | 1280 |

On the basis of the phosphorus analysis, the product had a 1000 mol. wt. and an average of about 4.6 tetradecene groups per phosphorus atom.

EXAMPLE VI

Synthesis of a Telomeric Hydrocarbyl Phosphonic Acid from a 4.6:1 Tetradecene:Dimethyl Phosphonate Telomer A 272 g. portion of the telomeric dimethyl hydrocarbyl phosphonate of Ex. V was converted to acid as in Examples II and IV by treatment with 200 ml. conc. HCl and 100 ml. water. The yield of product was 273 g. Analysis gave 3.1% P (3.18% calculated) and a TAN = 78 (vs. 114 calculated).

EXAMPLE VII

Telomeric Dimethyl Alkanephosphonate (from Hexene-1)

Benzoyl peroxide (2.3 g.) was added to a mixture of 47.5 g. (0.565 mole) hexene-1 and 4.15 g. (0.0376 mole) dimethyl phosphite at 25° C., and the mixture was refluxed under $N_2$ at 65° C. for 5½ hrs. Then 0.5 g. azobisisobutylronitrile (AIBN) were added at room temperature and the mixture was refluxed 2 hrs. at 65° C. Another 1.5 g. AIBN were added at 45° C., and the mixture was refluxed 28 hrs. more at 65° C. Then the mixture was refluxed at 75°–97° C. for 15 hrs. with 15–25 ml. of distillate continuously held back in a partially opened Dean-Stark trap. The reaction mixture was distilled to 110° C./atm. pressure and then to 220° C./10–15 mmHg. pressure to remove dimethyl hexanephosphonate and low boiling telomer (∼ 6 g. distillate). The 9 g. of higher telomers had a mol. wt. = 394 equivalent to the average composition,

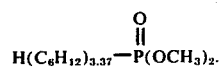

The distillate had mol. wt. = 232, equivalent to an average composition of $H(C_6H_{12})_{1.44}$—$P(OCH_3)_2$, which indicates some telomer had distilled with the n-hexanephosphonate.

EXAMPLE VIII

Telomeric Alkanephosphonic Acid from Hexene-1

The higher molecular weight telomeric ester (7.84 g.) of Example VII was refluxed for 5 hrs. at 71°–6° C. with 25 ml. benzene and 25 ml. conc. HCl. The mixture was extracted with ethyl ether, and the raffinate was water-washed. The ether was evaporated and the residual benzene solution was azeotroped free of water. Stripping to 180° C./∼ 20 mmHg. gave 7.13 g. product. The phosphorus analysis of 4.02% corresponds to approximately 770 mol. wt. = $H(C_6H_{12})_2$ — $PO_3H_2$.

EXAMPLE IX

Monomeric-Telomeric Mixture of Alkanephosphonic Acids from Octene-1

Benzoyl peroxide (4.0 g.) was added to a stirred mixture of octene-1 (112 g. (1.0 mole) and dimethyl phosphite (110 g./1.0 mole) at 117°–119° C. over 20 min., and this mixture was caused to react at 121°–185° C. over 4 hrs. followed by heating at 175° C. for 5½ hrs. The ester reaction mixture was hydrolyzed as in Example II, waterwashed, and stripped to ∼ 70° C./20 mmHg. Because of incomplete hydrolysis, this product was further hydrolyzed with aq. HCl in the presence of xylene at ∼ 90° F. for 6½ hrs. Separation of the xylene solution, water-washing, and stripping to ∼ 70° C. at <1 mmHg. gave 181 g. product with the following analysis:

| Found | Calculated for Octanephosphonic Acid |
|---|---|
| 10.8% | 16.0 |

The low phosphorus content indicates a significant amount of telomeric acid was present (the average number of octyl groups per phosphorus atom is about 2.0).

EXAMPLE X

Monomeric/Telomeric Mixture of Dimethyl Alkanephosphonate from Dodecene-1

Di-t-butylperoxide (16 g.) was added to a stirred mixture of dodecene-1 (672 g./4.0 moles) and dimethyl phosphite (440 g./4.0 moles) at 154°–160° C. over 3 hrs. The mixture was then heated 2 hrs. at 160° C. and 2 hrs. at 175° C.

A portion (~ 200 g.) of the reaction mixture was stripped to 120° C. at 20 mmHg., followed by further stripping at 70° C./<1 mmHg. The pot residue, 188 g., contained 7.35% P vs. 11.1% P calculated for the monomeric ester. The low phosphorus content indicates the average number of dodecyl groups per phosphorus atom is about 1.9.

The base fuel of the invention comprises a mixture of hydrocarbons boiling in the gasoline boiling range. This base fuel may consist of straight chain or branched chain paraffins, cycloparaffins, olefins and aromatic hydrocarbons or any mixture of these. This fuel can be derived from straight run naphtha, polymer gasoline, natural gasoline or from catalytically cracked or thermally cracked hydrocarbons and catalytically reformed stocks. The composition of the base fuel is not critical nor does the octane level of the base fuel have any material effect on the invention.

Any conventional motor fuel base may be employed in the practice of this invention. The base fuel may contain any of the additives normally employed in a motor fuel. For example, the base fuel may contain an anti-knock compound, such as tetraalkyl lead compound including tetraethyl lead, tetramethyl lead, tetrabutyl lead, mixtures thereof and the like. The tetraethyl lead mixture commercially available for automotive use contains an ethylene chloride-ethylene bromide mixture as a scavenger for removing lead from the combustion chamber in the form of a volatile lead halide. The motor fuel may also contain any of the conventional fuel additives including phenolic or amine antioxidants, metal deactivators, upper cylinder lubricants, and the like.

The telomeric alkane phosphonic acids of the invention are effective as carburetor anti-icing additives and as rust inhibitors in a concentration ranging from about 0.05 to 100 PTB, equivalent to about 0.00002 and 0.04 weight percent, respectively, of the fuel composition. The additive is surprisingly effective at a low concentration ranging from 0.0004 to 0.02 weight percent, amounts ranging from about 1 to 55 PTB (pounds of additive per 1000 barrels of fuel). The narrow preferred range is 2 to 10 PTB of the fuel composition. Fuel compositions containing less than about 10 PTB of the additive can come within the EPA indication of a "phosphorus-free" fuel composition (containing not more than 0.005 grams of phosphorus per gallon) depending on the phosphorus content of the telomer.

The base fuel which was utilized to test the properties of the telomeric alkane phosphorus compound of the invention was a premium grade gasoline consisting of about 27.5% aromatic, 8.5% olefinic, and 64.0% paraffinic hydrocarbons and boiled in the range of about 88° to 393° F. It has a research octane number of 100.4 and contained 2.95 cc. of tetraethyl lead per gallon. Blends were prepared consisting of the above base fuel mixed with specified amounts of the additive and then subjected to the following performance tests.

COLONIAL PIPELINE RUST TEST

A steel spindle, 3-3/16 inches long and ½ inch wide, made from ASTM D-665-60 steel polished with Crystal Bay fine emery paper, is used in the Colonial Pipeline Rust Test. The spindle was placed in a 400-cc. beaker with 300 cc. of fuel sample, which was maintained at 100° F. for one-half hour. Then 30 cc. of distilled water were added. The beaker and contents were kept at 100° F. for 3½ hours. The spindle was thereafter visually inspected and the percentage of rusted surface area was estimated. A rust result of 5% is a passing value.

The results of this test are given in Table I below:

TABLE I

COLONIAL PIPELINE RUST TEST

| Fuel Composition | Additive | Percent Rust (Duplicate runs) |
|---|---|---|
| 1. Base Fuel | None | 50, 75 |
| 2. Base Fuel | 1 PTB Example VI | 50, 75 |
| 3. Base Fuel | 2 PTB Example VI | 10, 25 |
| 4. Base Fuel | 4 PTB Example VI | 0.1–5, 5, 5–10 |
| 5. Base Fuel | 5 PTB Example II | 5, 5 |
| 6. Base Fuel | 8 PTB Example VI | 0.1, 5–10 |

The above test demonstrates that the fuel composition of the invention passes the rust test at additive concentrations above about 4 PTB.

CARBURETOR ICING TEST

The anti-icing properties of the additive-containing fuel of the invention were determined in a carburetor icing test. This test simulates an icing condition for a carbureted gasoline engine. The engine is replaced with a vacuum pump and the carburetor is replaced by a glass tube containing a simulated throttle plate. The test gasoline is aspirated into moisture-saturated cool air from an ice tower by means of a venturi created from a hypodermic needle. As the mixture passes the simulated throttle plate area, further cooling produces ice. Ice causes a pressure drop sensed by an inclined mercury manometer. Electronic timers record the seconds to reach a pressure drop across the throttle plate of about 0.5 inch and 0.9 inch of mercury. These values are correlated with actual engine stalling due to icing. The test is terminated if 300 seconds are reached. An effective carburetor anti-icing fuel additive is judged on the basis of a comparison with a blank (base fuel), because the level of numbers from this test tend to vary somewhat. The results of these tests are presented in the following table.

TABLE II

CARBURETOR ICING TEST

| Additive | Concentration PTB | Carburetor Icing Test Seconds 0.5"Hg | 0.9 Hg |
|---|---|---|---|
| 1. Blank (Base Fuel) | | 21–29 | 28–54 |
| 2. Example VI | 3 | 278,300+ | 300+,300+ |
| 3. Example VI | 4 | 300+,277 | 300+,300+ |
| 4. Example VI | 5 | 300+,300+ | 300+,300+ |

The above results demonstrate that the fuel composition of the invention is outstandingly effective in its carburetor icing properties.

The foregoing tests demonstrate a surprisingly effective fuel composition suitable for use under the prevailing regulations governing this class of materials.

We claim:

1. A motor fuel composition comprising a mixture of hydrocarbons in the gasoline boiling range and a surface active amount ranging from about 0.00002 to 0.04 weight percent based on said fuel composition of a telomeric phosphorus compound represented by the formula:

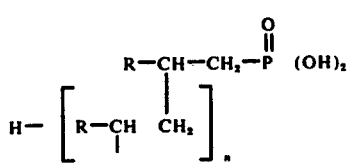

in which R is a hydrocarbyl radical having from 1 to 18 carbon atoms and *n* has a value from 1 to 25 with the average value for *n* being from 1 to 10.

2. A motor fuel composition according to claim 1 in which said telomeric phosphorus compound is represented by the formula:

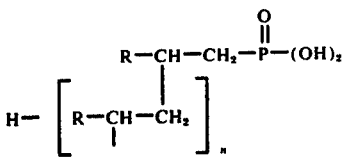

in which R is a hydrocarbyl radical having from 10 to 16 carbon atoms and *n* has an average value from 2 to 10.

3. A motor fuel composition according to claim 1 containing from about 0.0004 to 0.02 weight percent of said telomeric phosphorus compound.

4. A motor fuel composition according to claim 1 containing from about 0.0007 to 0.008 weight percent of said telomeric phosphorus compound.

* * * * *